United States Patent [19]
Mandal et al.

[11] Patent Number: 5,925,530
[45] Date of Patent: Jul. 20, 1999

[54] SIMPLE METHOD FOR THE DETECTION OF MINIMAL RESIDUAL DISEASE TO PREDICT RELAPSE OF ACUTE LYMPHOBLASTIC LEUKAEMIA

[75] Inventors: Chitra Mandal; Diviya Sinha; Dilip Kumar Bhattacharya, all of Calcutta, India

[73] Assignee: The Council of Scientifiic and Industrial Research, New Delhi, India

[21] Appl. No.: 08/824,159

[22] Filed: Mar. 26, 1997

[30] Foreign Application Priority Data

Nov. 15, 1996 [IN] India ............................ 2509/DEL/96

[51] Int. Cl.⁶ ..................... G01N 33/574; G01N 33/53; C12N 5/06
[52] U.S. Cl. ..................... 435/7.23; 435/7.24; 435/385
[58] Field of Search .................. 435/7.24, 7.23, 435/385

[56] References Cited

PUBLICATIONS

Sen G., et al. O–Acetylated Sialic Acid as a Distinct Marker for Differentiation Between Several Leukemia Erythrocytes (1994) Molecular Cellular Biochemistry 136: 65–70.

Tsai C–M, et al. A Waldenstrom Macroglobulin that is Both a Cold Agglutinin and a Cryoglobulin Because it Binds N–Acetylneuraminosyl (1977) Proc. Nat'l. Acad. Sci. 74: 4591–4594.

Sen G., et al. The Specificity of the Binding Site of Achatinin H, a Sialic Acid–Binding Lectin from *Achatina fulica* (1995) Carbohydrate Research 268: 115–125.

*Primary Examiner*—Toni R. Scheiner
*Attorney, Agent, or Firm*—John P. White; Cooper & Dunham LLP

[57] ABSTRACT

This invention relates to identification of a new key marker, namely, 9-O-Acetylated Sialoglycoconjugate with the help of a known 9-O-Acetylsialic acid binding lectin, AchatininH useful for the detection of minimal residual disease (MRD) and prediction of relapse by a lymphoproliferation assay in acute lymphoblastic leukaemia (ALL).

18 Claims, 2 Drawing Sheets

FIG. 2

Followup case profile of individual ALL patients under different phases of treatment. Relation between maximal lymphoproliferative dose of $ATN_H$ and % Recovery.

SIMPLE METHOD FOR THE DETECTION OF MINIMAL RESIDUAL DISEASE TO PREDICT RELAPSE OF ACUTE LYMPHOBLASTIC LEUKAEMIA

FIELD OF INVENTION

The present invention relates to a simple and effective method for the detection of minimal residual disease (MRD) and thereby identification or prediction of relapse by a lymphoproliferation assay in Acute lymphoblastic leukaemia (ALL). More specifically, the invention is for identification of a new key marker, namely, 9-O-Acetylated Sialoglycoconjugate with the help of a known 9-O-Acetylsialic acid binding lectin, AchatininH useful for the detection of minimal residual disease (MRD) and prediction of relapse by a lymphoproliferative assay in acute lymphoblastic leukaemia (ALL).

BACKGROUND OF THE INVENTION

The leukaemias are a heterogeneous group of neoplasms arising from the malignant transformation of heamatopoietic i.e. blood forming cells. Leukaemia can be broadly classified according to the cell type involved primarily (myeloid or lymphoid) and as acute or chronic depending on the natural history of the disease.

Acute lymphoblastic leukaemia (ALL) is the commonest type of leukaemia in childhood. It is a primarily a disease of children and young adults. It occurs in all races with a peak incidence in children between 3 to 5 years of age. Acute lymphoblastic leukaemia (ALL) is diagnosed in 2000 to 3000 new cases of childhood leukaemia in United States each year, whereas Acute myelogenous leukaemia (AML) is diagnosed in only 500 children and Chronic myeloid leukaemia (CML) is fewer than 100. About 40 million children in U.S.A. are affected under the group of 15 years, about ¾ Th. of these have ALL. (Nelson essential of Paedratics, 1990 Ed Bchrman RE and Klregman R pp. 53).

The causes are not known, but environmental agents including irradiation, chemical carcinogens, cytogenetic abnormalities and retrovirus infections are known to play an important role in the etiology of leukaemia. For instance, individuals with occupational/accidental radiation exposure, patients receiving radiation therapy or survivors of the atomic bomb explosions in Japan have a predictable and dose related increased incidence of leukaemia.

Pediatric haematopoietic malignancies rank first in cancer incidence and mortality in children and are responsible for roughly 40% of childhood related death (Carp and McCaffrey J. Natl. Cancer. Inst. 86, 1196, 1994).

In fact, the diagnosis and the treatment of Acute lymphoblastic leukaemia (ALL) is one of the major success stories of modern clinical oncology. For oncologists, Acute lymphoblastic leukaemia (ALL) represents a major therapeutic success as remission can be achieved in nearly 65% of patients (Pui and Crist Curr. Opinion on Oncology 7, 36, 1995, Lancet 374, pp 1783, 1996). With the available chemotherapeutic treatment, most of the Acute lymphoblastic leukaemia (ALL) patients can lead a normal disease free life for approximately 3–5 years. However, relapse and eventual treatment failure invariably occurs in most cases receiving identical treatment and this area is a major challenge for leukaemia specialists (Pui and Crist N. Eng. J. Med. 332, 1618, 1995). The reason behind the occurrence of relapse can be well understood if we take into consideration the definition adopted by the clinicians to state whether the patient has attained complete remission or not. The clinicians state:

a. If the laeukemia blasts in the bone marrow of the patients is less than 5% and
b. If no laeukemia blast is detected in the peripheral blood of patient, the patient is said to be in the state of apparently complete remission.

Therefore, the flaw lies in the definition itself since it states that leukaemic blast cells within a range of 0–5% may still be present within the patient when he is said to have attained the so called complete remission. At the time of diagnosis, the leukaemic cell mass is usually between $10^{11}$–$10^{12}$ cells and available chemotherapeutic agents produce a fractional cell kill capable of a 3 to 5 log kill resulting in the elimination of 99.99 to 99.999% of leukaemia cells. The remaining 0.01 to 0.001% leukaemic cells tantamounts to the persistence of $10^8$ to $10^9$ leukaemic blast cells respectively (Champlin and Golde Harrison Text book of Internal Medicine, 1552). What is important is that these persisting leukaemic blast cells are not detectable by standard morphology in bone marrow or peripheral blood. It is these cells that are responsible or relapse, if post induction chemotherapy fails to eradicate them. To eliminate this non-detectable yet existing leukaemic cell mass, maintenance therapy is given for an extended period (2 to 2.5 years) with the purpose of reducing the possible relapse and possibly eradicating this "iceberg" like leukaemic mass.

These residual laeukemia blasts remaining in the patient, which cannot be detected by the available techniques comprise the minimal residual disease (MRD) i.e. described as Phase B, C and D in results. It is the proliferation and infiltration of these blast cells which serves as the major cause of relapse. This "iceberg" is conventionally addressed as minimal residual disease (MRD) (Knechtli et. al. J. Clin Path 48, 1995). It is defined as the presence of leukaemic cells not detectable by morphology. Assays to detect minimal residual disease (MRD) is the need of the hour as these will help the clinicians to assess the effect of treatment on tumor burden and allow anticipation of relapse with greater precision (Brisco, Condan, Hughes, et. al. The Lancet 1994).

Therefore, the applicants have developed a simple blood based lymphoproliferative assay to detect minimal residual disease (MRD) and predict relapse in Acute lymphoblastic leukaemia (ALL) patients employing AchatininH as the tool.

PRIOR ART REFERENCES

Currently no specific marker is available to pin point the dose of chemotherapy and duration of maintenance therapy in acute lymphoblastic leukaemia (ALL).

Existing methods for the detection of leukaemic blasts cells are i) cytomorphology and karyotyping ii) immunological methods and iii) molecular detection:

Cytomorphology and karyotyping

Acquired non-random chromosomal translocation occurs in 30–70% of Acute lymphoblastic leukaemia (ALL) patients and can serve as marker of this disease. But the approach has limited sensitivity (1 to 5%) primarily due to the paucity of leukaemic blast cells during clinical remission (Campana D Pui Blood 85, 1416, 1995). Fluorescent in situ hybridization using chromosome specific or locus specific probes allows to identify abnormal ties in cells at metaphase (Leo Beau Blood, S1, 1979, 1993). Cytomorphology and Karyotyping techniques can detect one laeukemia blast in total population of 100 cells. Therefore they are said to have a sensitivity of 1% or $10^{-2}$.

Immunological methods

Immunological methods based on the recognition of leukaemia associated phenotypes not usually found in normal bone marrow have had promising results (Cole et. al. Baillieres Clin Haematol 7, 183, 1994). Immunophenotyping has been complimented by flow cytometric analysis where a combination of markers have been able to quantify minimal residual disease (MRD).

Main disadvantages:
1. Flow cytometric analysis can detect one laeukemia blast cell in a total cell population of 1000. So it is said to have a sensitivity of 0.1% or $10^{-3}$, which is inferior to available DNA based method (Huh and Andreef 8, 713, 1994, Meydan et al. Nature 379, pp 645, 1996).
2. The flow cytometer used for Flow cytometric analysis is very costly (about U.S. $1500) and not available in clinics.
3. It requires mandatory technical expertise.
4. The method needs expensive chemicals e.g. several specific antibodies and fluorescence conjugated chemicals.

Molecular approaches

In the majority of cases, relapse of acute lymphoblastic leukaemia is thought to involve the same leukaemic clone as the original disease (Bunin et. al. Leukaemia, 4, 722, 1990). Around 80% of cases of childhood acute lymphoblastic leukaemia are due to clonal expansion of precursor B cells and have rearrangement of IgH gene, from which specific DNA probes have been generated. Several PCR based methods (Brisco M J, Condan J, Hughes E, et al. The Lancet 19945; 343: 196–200, Veelken H, Tyeko B, Sklar J. Blood 1991: 78: 1318–1326, Wasserman R, Galili N, Ito J, et al. J of Clin. Oncol. 1992; 10: 1879–1880) have been reported for the detection of MRD in childhood acute lymphoblastic leukaemia (ALL).

These methods are based on the extraction of DNA from marrow and PCR amplification of tumor specific DNA or RNA sequences. The immunoglobulin heavy chain gene is used as a molecular marker to quantify leukaemic blast cells and N-ras gene to quantify total marrow cells. The number of amplifiable leukaemia and N-ras genes per ng of marrow DNA is calculated from Poisson's statistics and the level of minimal residual disease (MRD) is calculated from the ratio of the two heavy chains genes in each leukaemia cell and 2N-ras genes in each marrow cell. However, these published methods are successful in only half of the patients since different individuals can show different rearrangement of immunoglobulin genes or T cell Receptor genes.

The principle Drawbacks of the PCR methods for routine follow up of the MRD

Recently, the PCR methods have been developed to quantitate minimal residual disease (MRD) which detect the rearranged immunoglobulin or TCR genes in leukaemia cells (Brisco et al., 1994; Kuman, 1995). Employing the polymerase chain reaction, it has been shown that even one malignant cells per $10^5$ normal cells can be detected (O'Reilly et al., 1995). If both immunoglobulins and the T cell receptor gene rearrangements are studied, PCR has the potential to detect minimal residual disease (MRD) in nearly 90% of the cases for approximately one year despite clinical remission (Ito et al., 1994). However, technical and biological problems related to PCR exist, namely:

(i) occurrence of false positives due to contamination of reaction mix with previously employed samples
(ii) occurrence of false negatives results owing to degraded RNA or DNA or clonal evolution in approximately 20% of cases (Pui., 1995)
(iii) not all laeukemia specific IgH and TCR gene rearrangements are amenable to initial amplification of PCR using universal primers
(iv) a heterogeneous distribution of minimal residual disease (MRD) may result in sampling error since IgH and TCR gene rearrangements may be different in different individuals.
(v) these methods are costly, lengthy, very sophisticated and requiring mandatory technical expertise.

Since PCR undetectable residual disease is necessary for cures in most patients, it can be proposed that molecular remission defined as PCR undetectable disease is a milestone and target for achieving cure.

Evidently all these problems are unlikely to be exploited for commercial basis.

In India, the research in the field of acute lymphoblastic leukaemia (ALL) is mainly carried out at the Tata Memorial Hospital, Bombay. Their interest in acute lymphoblastic leukaemia is focused on cytogenesis (Gladstone et. al. Ind. J. Med. Res. 99, 264, 1994). Infection analysis (Raje et. al. Pediatr. Hematol. Oncol. 11, 271, 1994) and central nervous system relapse (Iyer et al. Leuk. Lymphoma, 13, 183, 1994).

Recently, a paper entitled 'O-acetylated sialic acid as a distinct marker for differentiation between several leukaemia erythrocytes.' Molecular and cellular Biochemistry 136: 65–70; 1994 mentions that a lectin (Achatinin H) isolated from the hemolymph of *Achatina fulica* snail, which has been shown to have narrow specificity towards 9O-acetyl sialic acid and this paper deals with identification of 9-O-acetylated glycoconjugates on erythrocytes only and nothing beyond. In addition, with reference to this publication of 1994, the following points must be taken into consideration:

1. As stated by the title, the paper identifies O-acetylated sialic acid as a distinct marker for differentiation between several leukemia erythrocytes only and not specifically to Acute lymphoblastic leukaemia (ALL). Therefore, it deals with the identification of O acetylated glycoconjugate on erythrocytes only.
2. The paper summarizes the result of a study of binding of AchatininH with erythrocytes of patients suffering from Acute lymphoblastic leukaemia (ALL) in their acute phase only.

Moreover, this paper does not describe or even envisage any experiment being performed with Peripheral blood mononuclear cells (PBMC) of these patients and accordingly had not addressed the problem of minimal residual disease and prediction of relapse.

3. In the above referred paper, very few patients (only five Acute lymphoblastic leukaemia (ALL) patients) have been included in the study and hence the result should not be considered as statistically significant.
4. In the above referred paper, the method is hemagglutination assay with erythrocytes but not the lymphoproliferation assay with peripheral blood mononuclear cells.
5. The study includes newly diagnosed Acute lymphoblastic leukaemia (ALL) patients who have not received any chemotherapeutic treatment. Thus, the preliminary work was only with the acute phase of the disease. This is nothing to do with the detection of minimal residual disease (MRD).
6. the hemogglutination assay with erythrocytes has also been performed with Acute lymphoblastic leukaemia (ALL) patients at different stages of treatment, i.e., Phases A, B, C, D and E no agglutination could be observed.

This clearly reflects that 9-O-acetylated glycoconjugates is transiently expressed or erythrocyte cell surface of only untreated Acute lymphoblastic leukaemia (ALL) patients (positive hemagglutination) but completely disappears with onset of treatment (no hemagglutination). Therefore, the transient expression of this 9-O-acetylated glycoconjugates on erythrocytes cannot predict minimal residual disease (MRD).

On the other hand, the present invention refers to the identification of 9-O-acetylated sialoglycoconjugates on peripheral blood mononuclear cells (PBMC) of children suffering from acute lymphoblastic leukaemia and not on their erthyocytes, detection of minimal residual disease in acute lymphoblastic leukaemia and prediction of relapse in acute lymphoblastic leukaemia, and the above features cannot be envisaged in the above publication.

An extensive world wide patent search has not shown any patent which claims that they can detect minimal residual disease (MRD) in Acute lymphoblastic leukaemia (ALL) using peripheral blood.

Presently patens filed in the area of diagnosis of leukaemias focus mainly on polymerase chain reaction methods namely:

1. Detecting minimal residual disease—in lymphoid malignancies using the polymerase chain reaction. Drawbacks are a) It is specific for lymphoid malignancies i.e. chronic and acute lymphoblastic leukaemia and not just ALL and it is PCR based.
2. BCL—3 gene sequences—used to detect cellular oncogenic C-myc translocation, leukaemia(s), and to monitor anti-neoplastic therapy. Drawbacks are a) It is not specific for acute lymphoblastic leukaemia buy any neoplastic transformation resulting due to C-myc oncogenic expression and is PCR based. Moreover detection of minimal residual disease (MRD) is not mentioned as per the method.
3. DNA encoding human common acute lymphoblastic leukaemia antigen-used for obtaining pure protein for diagnosis and treatment of medial-conditions. Drawbacks are the following a) The method is PCR based and detection of MRD is not mentioned as per the method.

Considering the drawbacks of the PCR methods as described in the prior art, development of a diagnostic assay which is simple, sensitive and specific is urgently required to detect and quantify Minimal residual disease (MRD) to control Acute lymphoblastic leukaemia (ALL) related sufferings.

To the best of our knowledge, there is presently no group, national or international who are studying detection and quantification of MRD employs the lectin AchatininH as a probe using peripheral blood. The selectivity of this lectin AchatininH has allowed not only the identification but also quantification of this residual blast or cancer cells using peripheral blood.

Sialic acids are a family of derivatives of N-acetyl or N-glycolyl neuraminic acids and are very important constituents of cell surface architecture. Sialic acids play an important role in receptors for virus, peptide hormones and toxins (Rosenberg A and Schengrund C L. Plenum Press, New York 1976). Sialic acids also functions as making agents on antigens, receptors and other recognition sites of the cell surface (Burness A T H. Animal Viruses, Chapman and Hall, New York 1981: Varki A Glycobiology 2, pp 25, 1992). The O substituted sialic acids exhibit species and tissue specific distribution in animals (Schauer R Adv. Carbohydr. Chem. Biochem. 1982: 40; 131). Changes in sialic and the degrees of O-acetylation of sialic acid residues have been reported in transformed and malignant cells.

Detection of sialic acid residues can be approached through the use of sialic acid specific lectins found in a variety of invertebrates (Mandal C and Mandal C Experientia 1990: 46; 433–441; Yeaton R W Dev. Comp. Immun. 1981: 5; 391) and serum (Tsai C M, Zopf D A, Yu R K, Wister R Jr., Ginsberg V Proc. Natl. Acad Sci. USA 1977: 74; 4591–4594).

AchatininH is a sialic acid binding lectin. This lectin has been prepared by allowing hemolymph to clot at room temperature, centrifugation for, separation of cells from the supernatant liquid, dialyzing using a known buffer containing calcium at a pH in the range of 8 and 9 and temperature in the range of 10–20° C., passing the dialyzed hemolymph through an affinity column containing a glycoprotein, which will bind the lectin contained in the dialyzed hemolymph, washing the column using a buffer to remove unwanted protein from the column and elution of the bound protein with a special buffer without calcium at a pH 8 to 9. This process has been described in our U.S. Pat. No. 165,730, Basu S, Sarkar M, Mandal C. Molecular and Cellular Biochemistry 1986; 71: 149–157). The lectin binds preferentially to sialic acid derivatives which are: (a) O-acetylated at the C-9 position of the parent molecule and (b) have an α2,6 linkage (Mandal C and Basu S. Biochem. Biophys Res Comm 1987; 148: 795–801, Sen G, Chowdhury M and Mandal C. Carbohydrate Research 1995, 268: 115–125). The selectivity of this lectin has been used for the study of ALL. This allowed us to identify a key marker (9-O-Acetyl Sialoglyco conjugate) on the PBMC surface which helped us to develop a rapid accurate and inexpensive process for diagnosis, detection of minimal residual disease (MRD) and prediction of relapse in Acute lymphoblastic leukaemia (ALL).

Sialic acid residues are commonly O-acetylated at the C-4, 7, 8 and 9 position of the parent molecule. Of these, 9-O acetylation occurs in very small amounts on normal lymphocytes and more importantly this 9-O acetylated sialoglycoconjugate is absent on normal human erythrocytes (Schauer R Adv. Carbohydr. Chem Biochem. 1982: 40; 131–234). Accordingly, we have exploited the selective binding of AchatininH to 9O acetylated derivatives (9-O AcSG) to serve as a diagnostic tool for detecting specific transformations on PBMC surface involving this biomarker. It has allowed us to identify the presence of 9O-AcSG on the cell surface of blast cells of the children suffering from acute lymphoblastic leukaemia (ALL), specially during maintenance therapy using a 9-O acetylated sialic acid binding lectin AchatininH.

The presence of 9O-AcSG has been corroborated by flurometric quantitative analysis of 9-O-acetylated sialic acid on the surface of PBMC.

SUMMARY OF THE INVENTION

Therefore, the invention provides an identification of a new key marker, namely, 9-O-Acetylated Sialoglycoconjugate with the help of a known 9O-Acetylsialic acid binding lectin, AchatininH useful for the detection of minimal residual disease (MRD) and prediction of relapse by a lymphoproliferation assay in acute lymphoblastic leukaemia (ALL).

OBJECTS AND DETAILED DESCRIPTION OF THE INVENTION

The main object of the present invention is to provide a simple and effective detection of Minimal Residual disease in Acute lymphoblastic leukaemia and thereby identifying or prediction of relapse by a lymphoproliferation assay.

Another object of the invention provides a process for identification of a new key marker, namely, 9-O-Acetylated Sialoglycoconjugate with the help a known 9-O-Acetylsialic acid binding lectin, AchatininH useful for the diagnosis of acute lymphoblastic leukaemia (ALL), detection of minimal residual disease (MRD) and prediction of relapse by a lymphoproliferation assay.

Yet another object of the present invention is to provide a process for the determination of a receptor on the cell surface of blast cells of the children suffering from acute lymphoblastic leukaemia (ALL) during maintenance therapy by a simple, specific, sensitive, non-invasive and economical, semi-automated colorimetric assay method which obviates the drawbacks as detailed above.

The proposed assay will allow for the assessment of the number of leukaemic blast cells either by a radioactive thymidine uptake lymphoproliferative assay method or by a simple, specific, sensitive, non-invasive and economical, semi-automated colorimetric assay method specially during maintenance therapy when the number of leukaemic blast cells are very low in the blood (less than 5%) and can not be detected by conventional methods.

Still another objective of the present invention is to provide a process for the quantification of leukaemic blast cell surface receptor which will reflect number of the leukaemic blast cells present in these children at different clinical stages of the disease. So, this invention provides an indicator as to when and how long chemotherapy should be continued. The process can predict the probability of relapse. So this invention will serve as an effective tool in the battle for identification of minimal residual laeukemia blast cells i.e. Minimal Residual Disease in children suffering from acute lymphoblastic leukaemia.

To meet the above objects, the present invention provides a simple, easy, sensitive, specific, effective and inexpensive method for the detection of MRD and prediction of relapse by identifying a key marker, i.e. cell surface receptor 9-O-acetylated sialoglycoconjugate" on the surface of peripheral blood mononuclear cells of acute lymphoblastic leukaemia patients, said method comprising collecting blood from acute lymphoblastic leukaemia patients at different clinical states of the disease; separating peripheral blood mononuclear cells by centrifugation; culturing them in tissue culture medium with AchatininH, harvesting the mononuclear cells and counting such cells and thereby diagnosing the disease, or pulsing such cultures with 3-(4,5-dimethylthiazole-2-yl)-2,5-diphenyltetrazolium bromide (MTT) for 4 hours before the termination of culture at 37° C., adding a solvent DMSO to dissolve the purple formazan crystals at the end of the incubation, and measuring the optical density at 560 nm with 690 nm reference in an ELISA reader, or the level of residual leukaemia cells (MRD) is determined by the optimal concentration of required for maximal proliferation.

Accordingly, the present invention provides for the identification of a new key marker, namely, 9-O-Acetylated Sialoglycoconjugate with the help of a known 9-O-Acetylsialic acid binding lectin, AchatininH useful for the detection of minimal residual disease (MRD) and prediction of relapse by a lymphoproliferation assay in acute lymphoblastic leukaemia (ALL) by a simple, specific, sensitive, non-invasive and economical, semi-automated colorimetric assay method. The applicants have designated this cell surface receptor at "9 O-acetylated sialoglycoconjugate" useful to reliably detect and quantify the small number of residual blast cells i.e. MRD, which comprises, collection of heparinised blood from acute lymphoblastic leukaemia patients (ALL) at different stages of the disease ii) separation of peripheral blood mononuclear cells (PBMC) by Ficoll Hypaque density centrifugation iii) seeding in triplicate at a density of $1\times10^5$ cells/well in RPMI 1640, supplemented with glutamine, penicillin, streptomycin and 10% heat inactivated human AB serum iv) culturing with 0.05–10 $\mu$g of the 9-O acetylated sialic acid binding lectin, AchatininH in 96 well flat bottom microtitre plates in a total volume of 250 $\mu$l, at 37° C. in a humidified atmosphere of 5% $CO_2$ and 95% air/v). After 4 days, cultures were pulsed with $^3$H Thymidine, 18 hours before the termination of culture. Cells were harvested and counts were taken. Alternatively, pulsing of the proliferative cells is performed by using 3-(4,5-dimethylthiazole-2-yl)-2,5-diphenyltetrazolium bromide (MTT).

In the present process, the whole blood is used for peripheral blood mononuclear cells operation and the 9-O-acetylsialic binding lectin, Achatinin H, purified from the hemolymph of *Achatina Fulica* snail is used as a unique reagent for stimulation of peripheral blood mononuclear cells in all experiments. Preferably, the concentration of AchatininH is used in the range of 0.05–10 $\mu$g for stimulation of peripheral blood mononuclear cells.

The culture medium used in the present process is selected from RPMI 1640, supplemented with glutamine, antibiotics and 10% heat inactivated human AB serum other medium such as DMEM and fetal calf serum and the culturing of the peripheral blood mononuclear cells is conducted in 96 well flat bottom microtitre plates, Tarson, Nunc, Costor or corning plates and sterile test tubes.

In a preferred aspect, 0.25 $\mu$l to 0.5 ml of a total reaction volume is used to culture peripheral blood mononuclear cells, the peripheral blood mononuclear cells are cultured at 37° C. in the presence of AchatininH and the peripheral blood mononuclear cells are being cultured in the presence of AchatininH in a humidified atmosphere of 5% $CO_2$ and 95% air.

In addition, the culture time of 4 days is used for maximum stimulation of peripheral blood mononuclear cells concentration of $1\times10^5$ cells/well gives best stimulation. Further, the cultures are regularly pulsed in 1 uCi of $^3$H thymidine or 0.05 uCi of $^3$H thymidine, 1 uCi of $^3$H thymidine which is added 18 hours before the termination of culture and 3-(4,5-dimethylthiazole-2-yl)-2,5-diphenyltetrazolium bromide (MTT) is added 4 hours before the termination of culture at 37° C. At the end of the incubation, solvent such as DMSO or SDS is added to dissolve the purple formazan crystals and the optical density is measured at 560 nm with 690 nm reference in an ELISA reader. The amount of formazan crystals produced which is proportional to the number of viable cells after cell proliferation is estimated colorimetrically and the dose of AchatininH ($\mu$g/$1\times10^5$ cells) needed for maximum proliferation of peripheral blood mononuclear cells is calculated.

The dose of AchatininH ($\mu$g/$1\times10^5$ cells) needed for maximum proliferation of peripheral blood cells been correlated with the status of the disease, increasing with progress of chemotherapy. The level of minimal residual leukaemia cells (MRD) is determined by the optimal concentration of AchatininH required for maximal proliferation.

To make the lymphoproliferative assay more rapid & convenient, conventional $^3$H thymidine uptake has been replaced by 3-(4,5-dimethylthiazole-2-yl)-2,5-diphenyltetrazolium bromide (MTT) 3-(4,5-dimethylthiazole-2-yl)-2,5-diphenyltetrazolium bromide (MTT) was added before the termination of culture at 37° C. followed by incubation. A solvent was added to dissolve the purple formazan crystals. The optical density was measured at 560 nm with 690 nm reference in an ELISA reader.

In order to clearly state the lymphoproliferative data, the design and the hypothesis behind the lymphoproliferative assay is stated in great details as follows:

(i) Peripheral blood mononuclear cells (PBMC) of Acute lymphoblastic leukaemia (ALL) patients, patients of other hematological disorders (AML, CML, NHL and Thalassemia) and normal donors were isolated by Ficoll Hypaque density centrifugation.

(ii) PBMC ($1 \times 10^5$ cells/well) were cultured with different concentrations of $Achatinin_H$ (0.05–10 ug) in Medium A for 96 hours at 37° C. with 5% $CO_2$ and 95% air.

(iii) The cultures were pulsed with $^3$H-Thymidine (1 uCi/well) for 18 hours.

(iv) The cells were harvested and counts taken in Rack Beta LKB liquid scintillation counter.

(v) For each patient and normal donor, the counts obtained were plotted in y axis against the $Achatinin_H$ dose plotted on x axis which ranged from 0.05–10 ug.

(vi) From this plot, the dose of $Achatinin_H$ at which maximal incorporation of radioactivity is obtained was determined. This has been designated as the maximal lymphoproliferative dose of $Achatinin_H$ for that patient and normal donor.

(vii) Accordingly, the mean of the maximal lymphoproliferative dose of $Achatinin_H$ for Acute lymphoblastic leukaemia (ALL) patients has been determined and compared with normal donors.

Interpretation of the lymphoproliferative assay

In a generalized way mitogen is any substance which stimulates cellular proliferation. A mitogen may be classified at potent for a particular cell type if, (i) Maximal proliferative dose of mitogen is very low and (ii) the density of the cell surface receptor to which the mitogen binds for mediating cellular proliferation is very high.

BRIEF DESCRIPTION OF THE ACCOMPANYING DRAWINGS

The drawings accompanying the specification comprising FIGS. 1 and 2 wherein

FIG. 1 shows the results of all the phases of the patients Acute lymphoblastic leukaemia (ALL) and FIG. 2 shows the percentage of recovery of individual patients in response to treatment.

FIG. 1 represents the dose of $Achatinin_H$ (X+SD ug/$1 \times 10^5$ cells) required for maximal lymphoproliferation of Acute lymphoblastic leukaemia (ALL) patients at different phases of treatment.

Figure 1:
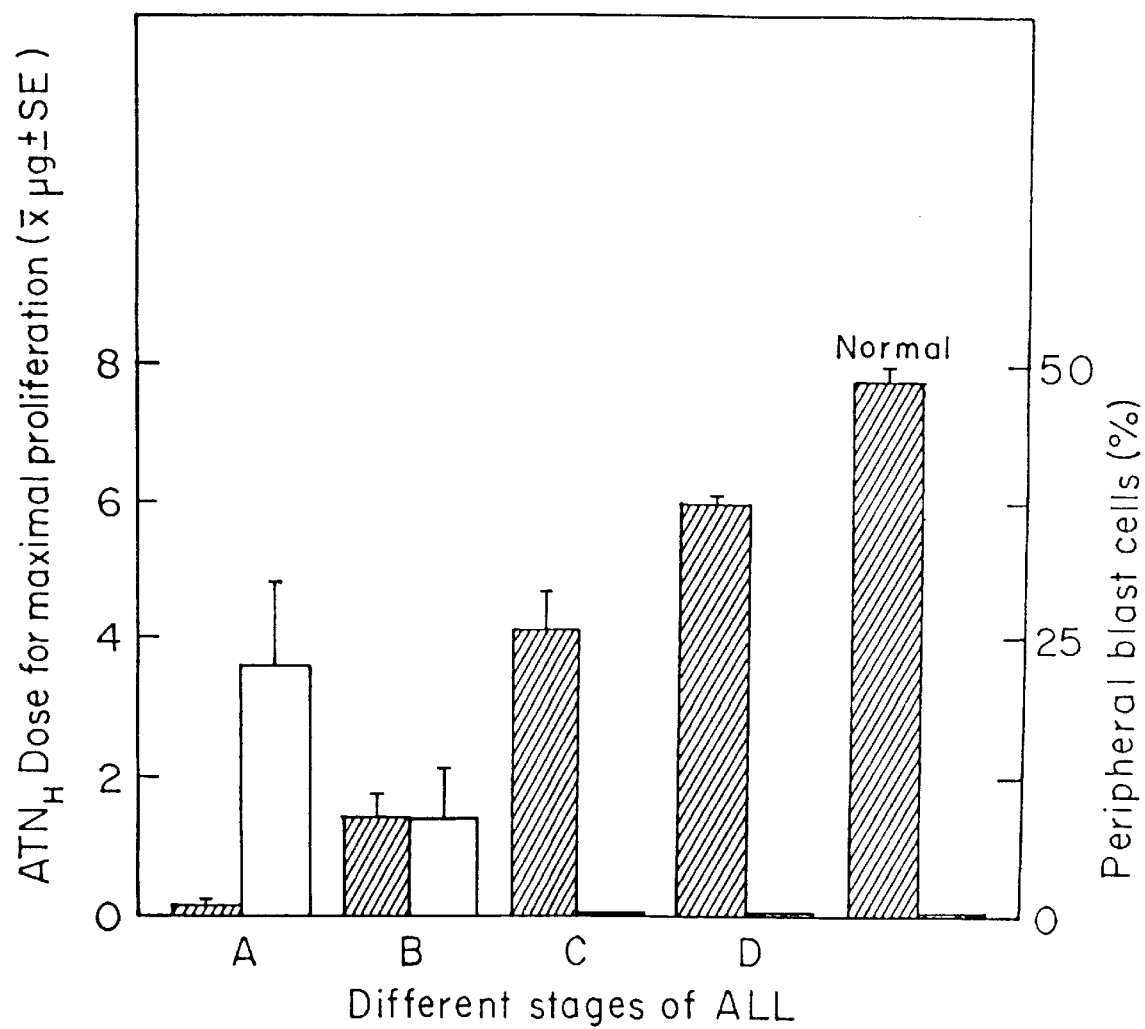

In Phase A (n=65, Male:Female=52:13), $Achatinin_H$ dose for maximal lymphoproliferation was 0.19+0.019 ug. Details of the individual patients data has been presented in Table 1.

Maximal lymphoproliferative dose of $Achatinin_H$ for Acute lymphoblastic leukaemia (ALL) patients is increased to 1.34+0.13 ug in Phase B (n=27, Male:Female=24:3). The table 2 describes the individual patients in phase B.

Maximal lymphoproliferative dose of $Achatinin_H$ for Acute lymphoblastic leukaemia (ALL) patients is further increased to 5.63+0.30 ug in Phase C (n=35, Male:Female=29:6) as described in Table 3.

Table 4 describes the individual patients of follow up studies and the maximal lymphoproliferative dose of $Achatinin_H$ for these patients is increased to 6.18+0.32 ug in Phase D (n=11, Male) compared to acute phase i.e. Phase A.

On contrary, with relapse (Phase E, n=8, Male:Female=6:2) maximal stimulatory dose of $Achatinin_H$ showed a sharp decline comparable to Phase A as predicted in Table 5.

Five different blood related (NHL, CML, AML, Thalassemmia and Aplastic anemia) served as negative controls showing no cross reactivity with Acute lymphoblastic leukaemia (ALL) by this invention process (Table 6).

PBMC of normal donors required an $Achatinin_H$ dose of 7.92+0.08 ug (n=25) for maximal lymphoproliferation (please see Table 7).

FIG. 1 summarizes the results of all the phases of the patients Acute lymphoblastic leukaemia (ALL) as described. From this study reflects a variation in the $Achatinin_H$ concentration for maximal lymphoblastic response pointing towards the differential expression of this key marker, a "9-O-acetylated sialoglycoconjugate", at different clinical stages of Acute lymphoblastic leukaemia (ALL) (FIG. 1). During Phase A, the key receptor is optimally expressed as shown by the lower $Achatinin_H$ concentration for maximal lymphoproliferation (FIG. 1). With progressive chemotherapy, either the expression of the receptor shows a marked decline or there occurs a masking of 9-O-acetyl sialic acid moieties of this receptor as evident from the increase in required dose of $Achatinin_H$ for maximal lymphoproliferation (FIG. 1). However, the $Achatinin_H$ dose for maximal lymphoproliferation shows a marked decline following relapse (Phase E, FIG. 1; Patient No. 2, 6, 7, 8 and 9 in FIG. 2), comparable with Phase A, reflecting the re-expression of this marker with relapse. Hence, the Achatinin$_H$ dose for maximal lymphoproliferation bears an inverse relationship with peripheral blast cell % (FIG. 1) and % Recovery of individual patients in response to treatment (FIG. 2) thereby serving as a reflection of Minimal Residual Disease (MRD).

Since the maximal lymphoproliferative dose of Achatinin$_H$ for ALL patients is significantly low in comparison to normal donors, we infer that mitogenic potential of Achatinin$_H$ in Acute lymphoblastic leukaemia (ALL) patients is significantly higher than that for normal donors. Moreover, since Achatinin$_H$ is a 9-O Acetyl sialic acid binding lectin lymphoproliferative assay it serves as an indirect measure of increased "9-O-acetylated sialoglycoconjugate" expression on PBMC surface of ALL patients in comparison to normal donors.

Therefore, the applicants identified that the 'maximal lymphoproliferative dose' of Achatinin$_H$ bears an inverse relationship with the expression of "9-O-acetylated sialoglycoconjugate" key marker on PBMC surface. The expression of this key marker serves as a direct reflection of laeukemia blast cells i.e. minimal residual disease (MRD) in Acute lymphoblastic leukaemia (ALL) patients and can predict relapse.

Thus the amount of AchatininH needed for maximum stimulation of peripheral blood mononuclear cells was determined. This allowed determination of the unique cell surface receptor, namely "9-O-acetylated sialoglycoconjugate" which could be exploited to reliably detect and quantify the small number of residual blast cells i.e. MRD which stay in peripheral blood even after chemotherapy. So, it can serve as an index to determine the dose and duration for which maintenance therapy should be continued to achieve complete cure. Thus its correlation with the status of the disease was assessed.

In a preferred embodiment of the invention, following are the possible permutations and combinations of the above mentioned process:

Whole heparinised blood is used for peripheral blood mononuclear cell separation. Alservers solution or any anti-coagulant can be used for collection of blood. The concentration of AchatininH can vary in the range of 0.1 to 10 μg in 0.85% saline or tissue culture medium. Other buffers such as This hydrochloride buffer, can also be used. 96 well U bottom microtitre plates are used for lymphoproliferation assay. 96 well V shaped microtitre plates can also be used. Sterile Tarson (indigenous) or Nunc or Coaster or corning plates are equally good. Small glass or plastic tubes also can be used. The total reaction volume is 0.25 ml for lymphoproliferation assay. The volume can be varied from 0.2–0.5 ml for lymphoproliferation assay. Peripheral blood mononuclear cell have been incubated at 37° C. in presence of AchatininH. The temperature can be varied from 30° C. to 38° C. Whole reaction was carried out in presence of 30 mM of $Ca^{2+}$. However, the concentration of $Ca^{2+}$ can be varied from 25 to 30 mM. The reaction time of 96 hours was used for maximum proliferation. The time may be varied from 24 to 72 hours. The amount of AchatininH needed for maximum proliferation did not change even if the cells were allowed to proliferate only for 24 hours. However, a reduction in the count was observed. Peripheral blood mononuclear cells ($1 \times 10^5$) were cultured in triplicates. The number of peripheral blood mononuclear cells can be varied from $1 \times 10^3$ to $1 \times 10^5$ cells. However, culture time of 96 hours and cell concentration $1 \times 10^5$ gave best lymphoproliferation. Radioactive thymidine can be used from 0.5 to 1 uCi. Instead of radioactive thymidine, culture can be pulsed with MTT 4 hours before the termination of culture at 37° C. At the end of the incubation, a solvent, DMSO, is added to dissolve the purple formazan crystals. Any other solvent e.g. sodium dodecyl sulphate or combination of sodium dodecyl sulphate and hydrochloric acid or dimethyl sulfoxide or propanol or ethanol can be used to dissolve the purple formazan crystals. The optical density is measured at 560 nm with 690 nm reference in an ELISA reader to assess the lymphoproliferation.

The following examples are given by a way of illustration of the present invention and these should not be construed to limit the scope of the present invention:

EXAMPLE 1

Approximately 2–3 ml of blood was collected from acute lymphoblastic leukaemia patients (n=40). Peripheral blood mononuclear cells were separated by Ficoll Hypaque density centrifugation and seeded at a density of $1 \times 10^5$ cells/well in RPMI 1640, supplemented with glutamine, penicillin, streptomycin and 10% heat inactivated human AB serum. Cell viability was more than 95% as checked by their ability to exclude Trypan blue dye (0.2%). Peripheral blood mononuclear cells were cultured in triplicates ($1 \times 10^5$ cells/well) with different concentration of AchatininH (0.05 to 10 μg) in 96 well flat bottom microtitre plates in a total volume of 250 μl, at 37° C. in a humidified atmosphere of 5% $CO_2$ and 95% air. A culture time of 4 days and cell concentration of $1 \times 10^5$ cells/well showed best results. Cultures were pulsed with 1 uCi of $^3$H Thymidine, 18 hours before the termination of culture. Cells were harvested and counts were taken.

EXAMPLE 2

Approximately 2–3 ml of blood was collected from acute lymphoblastic leukaemia patients (n=50). Peripheral blood mononuclear cells were separated by Ficoll Hypaque density centrifugation and seeded at a density of $1 \times 10^4$ cells/wells in RPMI 1640 (it is a trade name), supplemented with glutamine, gentamycin and 10% heat inactivated human AB serum. Cell viability was more than 95% as checked by their ability to exclude Trypan blue dye (0.2%). Peripheral blood mononuclear cells were cultured in triplicates ($1 \times 10^4$ cells/well) with different concentration of AchatininH (0.05–10 μg) in 96 well flat bottom microtitre plates in a total volume of 250 μl, at 37° C. in a humidified atmosphere of 8% $CO_2$ and 95% air. Cultures were pulsed with 1 uCi of $^3$H Thymidine, 18 hours before the termination of culture after culturing the cells for 3 days. Cells were harvested and counts were taken.

EXAMPLE 3

Approximately 2–3 ml of blood was collected from acute lymphoblastic leukaemia patients (n=30). Peripheral blood mononuclear cells were separated by Ficoll Hypaque density centrifugation and seeded at a density of $1 \times 10^5$ cells/well in RPMI 1640, supplemented with glutamine, antibiotics and 10% heat inactivated human AB serum. Cell viability was more than 95% as checked by their ability to exclude Trypan blue dye (0.2%). Peripheral blood mononuclear cells were cultured in triplicates ($1 \times 10^5$ cells/well) with different concentration of AchatininH (0.05–10 μg) in 96 well flat bottom microtitre plates in a total volume of 250 μl at 37° C. in a humidified atmosphere at 5% $CO_2$ and 95% air for 4 days. Cultures were pulsed, with MTT 4 hours before the termination of culture at 37° C. At the end of the incubation, a solvent DMSO was added to dissolve the purple formazan crystals. The optical density was measured at 560 nm with 690 nm reference in an ELISA reader.

EXAMPLE 4

Approximately 2–3 ml of blood was collected from acute lymphoblastic leukaemia patients (n=26). Peripheral blood mononuclear cells were separated by Ficoll Hypaque density centrifugation and seeded at a density of $1 \times 10^4$ cells/well in RPMI 1640, supplemented with glutamine, gentamycin and 10% heat inactivated human AB serum. Cell viability was more than 95% as checked by their ability to exclude Trypan blue dye (0.2%). Peripheral Blood mononuclear cells were cultured in triplicates ($1 \times 10^5$ cells/well) with different concentrations of AchatininH (0.05–10 μg) in 96 well flat bottom microtitre plates in a total volume of 250 μl, at 37° C. in a humidified atmosphere of 5% $CO_2$ and 95% air for 3 days. Culture were pulsed with MTT 4 hours before the termination of culture at 37° C. At the end of the incubation, a solvent DMSO was added to dissolve the purple formazan crystals. The optical density was measured at 560 nm with 690 nm reference in an ELISA reader.

The lymphoproliferation assay carried out according to the process of the present invention (examples 1–4) has been identified as an accurate method for the identification of anew key marker, namely, 9-O-Acetylated Sialoglycoconjugate with the help of a known 9-O-Acetylsialic acid binding lectin, AchatininH useful for the diagnosis of acute lymphoblastic leukaemia (ALL), detection of minimal residual disease (MRD) and prediction of relapse and has following properties:

The level of residual leukaemia cells i.e. minimal residual disease (MRD) was determined by the optimal concentration of AchatininH required for maximal proliferation. This invention process clearly demonstrates that a key marker is expressed at a very high concentration during acute phase, Phase A, as indicated by the low dose of AchatininH (0.19±0.02 μg) needed for maximum proliferation of peripheral blood mononuclear cells (Table 1). It showed a decrease expression following treatment, Phase B, as indicated by the distinct increase in the dose of AchatininH ranging from 1.34±0.13 μg (Table 2). During maintenance therapy, Phase C (Table 3) and follow up, Phase D (Table 4), no blast cell was observed in the peripheral blood indicating normal blood picture. This invented process still can observe stimulation indicating the presence of some key marker i.e. cell surface receptor—"9-O-acetylated sialoglycoconjugate" on the surface of peripheral blood mononuclear cells. The dose of AchatininH required was 5.63±0.3 μg during maintenance therapy (Table 3) which was not equivalent to normal peripheral blood mononuclear cells. So despite the normal, clinical blood picture, the patients under maintenance therapy and follow up still consist of residual leukaemic cells i.e. minimal residual disease (MRD) (Phase C, D, E in Table 3, 4, 5) from the decline in the dose of AchatininH. Five different blood related diseases (NHL, CML, AML, Thalassemia and Aplastic anemia) served as negative controls showing no cross reactivity with Acute lymphoblastic leukaemia (ALL) by this invention process (Table 6). 25 normal human volunteers of different ages, having different blood groups showed AchatininH dose of 7.92±0.08 μg (Table 7) as compared to Acute lymphoblastic leukaemia (ALL) patients under different phases of treatment. Relapse (Table 5) could be successfully predicted by determining the alteration in maximal lymphoproliferative dose of AchatininH of these patients at different stages of the disease.

RESULTS OF INDIVIDUAL PATIENTS

Study included 192 human blood samples. All these patients were divided according to their duration of treatment.

TABLE 1

| PHASE A (0–4 weeks treatment/first remission) | | | |
|---|---|---|---|
| Patient No | Sex, Age (Year) | Treatment (weeks). | Peripheral blast cell (%). | Maximal lymphoproliferative dose of AchatininH. |
| 1. | M, 6 | 0 | 84 | 0.1 |
| 2. | M, 3.5 | 0 | 30 | 0.1 |
| 3. | M, 5 | 0 | 24 | 0.1 |
| 4. | M, 3 | 1 | 20 | 0.25 |
| 5. | M, 8 | 0 | 60 | 0.1 |
| 6. | M, 5 | 0 | 50 | 0.1 |
| 7. | M, 5 | 2 | 4 | 0.1 |
| 8. | M, 5 | 2 | 25 | 0.25 |
| 9. | M, 5 | 0 | 25 | 0.25 |
| 10. | M, 2.5 | 0 | 80 | 0.5 |
| 11. | M, 2.5 | 0 | 38 | 0.5 |
| 12. | M, 6 | 0 | 64 | 0.1 |
| 13. | F, 5 | 4 | 10 | 0.1 |
| 14. | M, 5 | 1 | 30 | 0.1 |
| 15. | M, 5 | 0 | 38 | 0.1 |
| 16. | M, 3 | 1 | 30 | 0.5 |
| 17. | M, 7 | 4 | 10 | 0.5 |
| 18. | M, 6 | 4 | 3 | 0.1 |
| 19. | M, 6 | 0 | 84 | 0.5 |
| 20. | M, 5 | 2 | 7 | 0.25 |
| 21. | M, 3.5 | 1 | 40 | 0.25 |
| 22. | M, 5 | 2 | 30 | 0.5 |
| 23. | M, 6 | 0 | 80 | 0.1 |
| 24. | F, 13 | 0 | 60 | 0.25 |
| 25. | F, 7.5 | 0 | 34 | 0.1 |
| 26. | M, 3 | 1 | 49 | 0.1 |
| 27. | M, 5 | 0 | 54 | 0.1 |
| 28. | M, 3.5 | 1 | 40 | 0.25 |
| 29. | F, 8 | 0 | 60 | 0.1 |
| 30. | F, 7.5 | 0 | 38 | 0.25 |
| 31. | M, 8 | 0 | 80 | 0.1 |
| 32. | M, 3.5 | 4 | 40 | 0.1 |
| 33. | M, 6 | 0 | 58 | 0.1 |
| 34. | M, 1.5 | 0 | 95 | 0.1 |
| 35. | F, 7.5 | 2 | 25 | 0.25 |
| 36. | M, 4 | 1 | 22 | 0.1 |
| 37. | M, 6 | 0 | 63 | 0.1 |
| 38. | M, 3.5 | 0 | 74 | 0.1 |
| 39. | M, 3.5 | 1 | 12 | 0.25 |
| 40. | M, 4 | 2 | 42 | 0.1 |
| 41. | M, 3.5 | 4 | 10 | 0.1 |
| 42. | M, 5 | 4 | 7 | 0.25 |
| 43. | M, 5 | 0 | 81 | 0.1 |
| 44. | M, 5 | 0 | 33 | 0.1 |
| 45. | M, 5 | 4 | 5 | 0.5 |
| 46. | F, 7 | 0 | 55 | 0.1 |
| 47. | M, 7.5 | 0 | 57 | 0.1 |
| 48. | F, 7 | 0 | 39 | 0.1 |
| 49. | F, 7 | 0 | 63 | 0.1 |
| 50. | F, 7 | 0 | 51 | 0.1 |
| 51. | M, 4 | 0 | 90 | 0.1 |
| 52. | F, 5 | 0 | 39 | 0.1 |
| 53. | M, 6 | 1 | 51 | 0.1 |
| 54. | M, 3 | 0 | 60 | 0.1 |
| 55. | M, 8 | 1 | 57 | 0.1 |
| 56. | M, 12 | 0 | 73 | 0.1 |
| 57. | F, 9 | 3 | 44 | 0.1 |
| 58. | M, 5 | 2 | 29 | 0.25 |
| 59. | M, 2.5 | 0 | 22 | 0.1 |
| 60. | M, 6 | 0 | 57 | 0.1 |
| 61. | F, 5 | 0 | 82 | 0.1 |
| 62. | M, 7 | 0 | 53 | 0.1 |
| 63. | M, 5 | 4 | 10 | 1.0 |
| 64. | M, 7 | 4 | 9 | 0.25 |
| 65. | M, 2 | 0 | 79 | 0.1 |

Result

Phase A comprised of 65 Acute lymphoblastic leukaemia (ALL) patients. The mean (X±SE) of the 'maximal lymphoproliferative dose' of AchatininH was 0.19±0.019 μg/1× $10^5$ cells reflecting a significantly high level of 9 O-acetylated sialoglycoconjugate" on the surface of peripheral blood mononuclear cells during Phase A. A blast cell % of 45.1±2.97 was observed in Phase A. Therefore the 'maximal lymphoproliferative dose of AchatininH' bears an inverse relationship with the expression of 9 O-acetylated sialoglycoconjugate" on the surface of peripheral blood mononuclear cells (PBMC). This indicates that the lesser the 'maximal lymphoproliferative dose of AchatininH' the more is the expression of 9 O-acetylated sialoglycoconjugate" on the surface of peripheral blood mononuclear cells. The level of 9 O-acetylated sialoglycoconjugate" on the surface of peripheral blood mononuclear cells, as indicated by the 'maximal lymphoproliferative dose of AchatininH', serves as a direct reflection of % blast cells i.e. acuteness of the disease. Thus the phase of treatment of Acute lymphoblastic leukaemia (ALL) patients could be diagnosed by this invented method.

TABLE 2

PHASE B (4–8 weeks treatment/early intensification).

| Patient No. | Sex, Age (years). | Treatment (weeks). | Peripheral blast cell (%). | Maximal lymphoproliferative dose of AchatininH. |
|---|---|---|---|---|
| 1. | M, 6 | 5 | 0 | 2.0 |
| 2. | M, 5 | 6 | 2 | 0.25 |
| 3. | M, 8 | 7 | 0 | 1.0 |
| 4. | M, 7 | 8 | 2 | 2.0 |
| 5. | M, 5 | 6 | 2 | 2.0 |
| 6. | F, 7 | 4 | 2 | 0.5 |
| 7. | M, 12 | 5 | 10 | 1.0 |
| 8. | M, 6 | 6 | 0 | 1.0 |
| 9. | M, 5 | 7 | 3 | 1.0 |
| 10. | M, 12 | 8 | 0 | 2.0 |
| 11. | M, 12 | 5 | 0 | 1.0 |
| 12. | M, 5 | 6 | 3 | 2.0 |
| 13. | M, 5 | 7 | 0 | 2.0 |
| 14. | M, 3 | 5 | 2 | 2.0 |
| 15. | F, 5 | 5 | 0 | 1.0 |
| 16. | M, 14 | 5 | 0 | 1.0 |
| 17. | M, 4 | 7 | 2 | 1.0 |
| 18. | M, 5 | 5 | 2 | 1.0 |
| 19. | M, 5 | 6 | 2 | 2.0 |
| 20. | M, 6 | 6 | 0 | 0.5 |
| 21 | M, 7 | 4 | 0 | 0.5 |
| 22. | M, 6 | 4 | 3 | 3.0 |
| 23. | M, 7 | 4 | 0 | 2.0 |
| 24. | M, 5 | 5 | 0 | 0.5 |
| 25. | M, 7 | 7 | 0 | 1.0 |
| 26. | M, 14 | 8 | 0 | 1.0 |
| 27. | F, 11 | 8 | 0 | 2.0 |

Result

Phase B comprised of 27 ALL patients and the 'maximal lymphoproliferative dose of AchatininH' (X±SE) increased to 1.34±0.13 ug reflecting a decline in the expression of the key marker, namely, 9 O-acetylated sialoglycoconjugate" on the surface of peripheral blood mononuclear cells. The different between the 'maximal lymphoproliferative dose of AchatininH' in Phase A and Phase B was statistically significant (p<0.0005). The mean blast cell % of 0.3±0.4 in Phase B reiterates a relationship between the expression 9 O-acetylated sialoglycoconjugate" on the surface of peripheral blood mononuclear cells and the acuteness of the disease. Thus chemosensitivity of ALL patients could be detected by this invented process.

TABLE 3

PHASE C (8 weeks–2.5 years treatment/maintenance therapy).

| Patient No. | Sex, Age (years). | Treatment (weeks). | Maximal lymphoproliferative dose of AchatininH. |
|---|---|---|---|
| 1. | F, 11 | 12 | 2.0 |
| 2. | M, 5 | 8 | 3.0 |
| 3. | M, 6 | 7 | 4.0 |
| 4. | M, 5 | 24 | 4.0 |
| 5. | M, 8 | 19 | 6.0 |
| 6. | M, 8 | 21 | 6.0 |
| 7. | F, 11 | 12 | 2.0 |
| 8. | M, 6 | 24 | 6.0 |
| 9. | M, 5 | 24 | 3.0 |
| 10. | M, 8 | 19 | 6.0 |
| 11. | F, 10 | 35 | 6.0 |
| 12. | M, 5 | 12 | 6.0 |
| 13. | M, 7.5 | 34 | 6.0 |
| 14. | F, 12 | 42 | 6.0 |
| 15. | M, 12 | 9 | 2.0 |
| 16. | M, 14 | 47 | 8.0 |
| 17. | M, 8 | 22 | 8.0 |
| 18. | M, 5 | 24 | 6.0 |
| 19. | M, 7 | 32 | 4.0 |
| 20. | F, 14 | 48 | 6.0 |
| 21. | M, 6 | 60 | 6.0 |
| 22. | M, 6 | 50 | 6.0 |
| 23. | M, 6 | 62 | 6.0 |
| 24. | M, 7 | 28 | 6.0 |
| 25. | M, 7 | 44 | 8.0 |
| 26. | M, 8 | 48 | 8.0 |
| 27. | M, 12 | 51 | 6.0 |
| 28. | M, 12 | 51 | 8.0 |
| 29. | M, 5 | 11 | 3.0 |
| 30. | M, 5 | 33 | 8.0 |
| 31. | F, 5 | 44 | 8.0 |
| 32. | M, 14 | 23 | 4.0 |
| 33. | M, 14 | 15 | 4.0 |
| 34. | M, 7 | 9 | 8.0 |
| 35. | M, 8 | 22 | 8.0 |

Result

Phase C included 35 ALL patients. The mean (X±SE) of the 'maximal lymphoproliferative dose of AchatininH' is $5.63 \pm 0.30 / 1 \times 10^5$ cells. Hence the 'maximal lymphoproliferative dose of AchatininH' shows a progressive increase with treatment reflecting a decline in the expression of 9 O-acetylated sialoglycoconjugate" on the surface of peripheral blood mononuclear cells with treatment. However, it must be noted that although no blast cells could be detected by available methods, the 'maximal lymphoproliferative dose of AchatininH', even in maintenance therapy, was significantly less as compared to normal donors (Table 7). Thus the 9 O-acetylated sialoglycoconjugate" on the surface of peripheral blood mononuclear cells expression in maintenance therapy is significantly higher than normal donors. The 9 O-acetylated sialoglycoconjugate" on the surface of peripheral blood mononuclear cells expression serves as direct reflection of blast cell % and minimal residual disease (MRD) can be detected by this invented process.

TABLE 4

PHASE D (patients followed up after completion of maintenance therapy).

| Patient No. | Sex, Age (years). | Treatment (weeks). | Maximal/ lymphoproliferative dose of AchatininH. |
|---|---|---|---|
| 1. | M, 5 | 88 | 6.00 |
| 2. | M, 6.5 | 96 | 6.00 |
| 3. | M, 8 | 96 | 4.00 |
| 4. | M, 5 | 96 | 6.00 |
| 5. | M, 5 | 136 | 6.00 |
| 6. | M, 6.5 | 126 | 6.00 |
| 7. | M, 5 | 120 | 6.00 |
| 8. | M, 8 | 150 | 6.00 |
| 9. | M, 8 | 136 | 6.00 |
| 10. | M, 8 | 192 | 8.00 |
| 11. | M, 7 | 208 | 8.00 |

Results

Phase D included 11 patients who were followed up after completion of maintenance therapy. The mean (X±SE) of the 'maximal lymphoproliferative dose of AchatininH' was 6.18±0.32 ug/1×10$^5$ cells, which was significantly less in comparison to normal donors (Table 7) reflecting the persistence of the blast cells by this method. Thus MRD could be detected by this invented process.

TABLE 5

RELAPSE CASES (patients for which relapse could be successfully predicted by our invented assay).

| Patient No. | Sex, Age (Years). | Time at which relapse occurred. | Maximal lymphoproliferative dose of AchatininH$_H$. | Remarks. |
|---|---|---|---|---|
| 1. | F, 7.5 | One Year after the completion of maintenance therapy | 0.25 | Relapse predicted by the invented patent. |
| 2. | F, 7.5 | " | 0.25 | " |
| 3. | M, 7 | During maintenance therapy. | 1.0 | " |
| 4. | M, 5 | One Year after maintenance therapy | 0.1 | " |
| 5. | M, 14 | Six months after maintenance therapy. | 1.0 | " |
| 6. | M, 5 | After maintenance therapy. | 2.0 | " |
| 7. | M, 7 | During maintenance therapy. | 0.25 | " |
| 8. | M, 5 | " | 3.0 | " |

Result

The decreased in 'maximal lymphoproliferative dose of AchatininH' indicates the reexpression of 9 O-acetylated sialoglycoconjugate" on the surface of peripheral blood mononuclear cells. The expression of 9 O-acetylated sialoglycoconjugate" is more as compared to that maintenance therapy (Table 3) and follow-up (Table 4). Thus decreased in 'maximal lymphoproliferative dose of AchatininH' indicates the reexpression of 9 O-acetylated sialoglycoconjugate" on the surface of peripheral blood mononuclear cells and could predict relapse in these patients. Our prediction correlated well with the clinical observation.

TABLE 6

Results of patients studied for cross reactivity

| Patient No. | Sex, Age (Years). | Disease. | Response to AchatininH. |
|---|---|---|---|
| 1. | M, 12 | Thalassemmia | 8.00 |
| 2. | M, 12 | " | 8.00 |
| 3. | M, 5 | " | 8.00 |
| 4. | M, 5 | " | 8.00 |
| 5. | M, 10 | NHL | 8.00 |
| 6. | M, 7 | AML | No response |
| 7. | M, 7 | AML | " |
| 8. | F, 11 | NHL | " |
| 9. | M, 38 | CML | " |
| 10. | M, 35 | CML | " |
| 11. | M, 42 | CML | " |
| 12. | F, 40 | CML | " |
| 13. | M, 33 | CML | " |
| 14. | F, 9 | AML | " |
| 15. | M, 5 | AML | " |
| 16. | M, 48 | CML | " |
| 17. | M, 7 | Aplastic anemia | " |
| 18. | M, 5 | " | " |
| 19. | F, 8 | Thalassemmia | 8.00 |
| 20. | M, 12 | NHL | 8.00 |
| 21. | M, 8 | NHL | 8.00 |

Results

In Thalassemmic and NHL (Non Hodgkin's Lymphoma) patients the maximal lymphoproliferative dose of AchatininH' was similar to normal human donors (Table 7). No lymphoproliferation was observed in CML (Chronic Myelogenous Leukemia), AML (Acute Myelogenous Leukemia) and Aplastic Anemia patients. Thus patients of other diseases (NHL, CML, AML, Thalassemmia and Aplastic Anemia) served as negative controls showing no cross reactivity with ALL by this invented process.

TABLE 7

Response of the normal donors

| Normal donors. | Sex, Age (Years). | Blood Groups. | Maximal lymphoproliferative dose of AchatininH. |
|---|---|---|---|
| 1. | F, 24 | A+ | 8.00 |
| 2. | M, 10 | ND. | 8.00 |
| 3. | M, 15 | " | 8.00 |
| 4. | F, 24 | A+ | 8.00 |
| 5. | M, 23 | B− | 8.00 |
| 6. | M, 25 | 0+ | 8.00 |
| 7. | F, 41 | A+ | 8.00 |
| 8. | M, 36 | 0+ | 8.00 |
| 9. | M, 5 | ND | 6.00 |
| 10. | F, 25 | A+ | 8.00 |
| 11. | F, 25 | " | 8.00 |
| 12. | F, 41 | " | 8.00 |
| 13. | F, 25 | " | 8.00 |
| 14. | F, 25 | " | 8.00 |
| 15. | F, 41 | " | 8.00 |
| 16. | M, 12 | ND | 8.00 |
| 17. | M, 38 | O+ | 8.00 |
| 18. | F, 24 | ND | 8.00 |
| 19. | M, 11 | ND | 8.00 |
| 20. | M, 15 | ND | 8.00 |
| 21. | M, 24 | ND | 8.00 |
| 22. | M, 26 | ND | 8.00 |
| 23. | M, 9 | ND | 8.00 |
| 24. | F, 41 | A+ | 8.00 |
| 24. | F, 26 | A+ | 8.00 |

Results 25 normal human volunteers of different ages, having different blood groups were included in study. The mean (X±SE) of the 'maximal lymphoproliferative dose of AchatininH' was 7.92±0.08 ug/1×10$^5$ cells, reflecting a very low expression of 9-O Acetyl Sialo Glyco conjugate on PBMC surface of normal donors as compared to ALL patients under different phases of treatment.

The salient advantages of the proposed invention are
  (a) A simple, rapid and easy, method employing peripheral blood (2–3 ml of blood per patients) It requires peripheral blood as the starting material in place of bone marrow.
  (b) The abundant availability of *Achatina Fulica* snail and single step purification with high yield (6% and its restricted specificity (Mandal C, Basu S. Biochem Biophys Res Commun 1987; 148: 795–801, Sen G, Mandal C. Carbohydrate Research 1995; 268: 115–125) makes it, useful tool for biochemical anaylsis. The lectin also has long term stability for >2 years and can be stored at 6° C.–10° C. in a filter sterilized condition at a concentration of 1 mg/ml.
  (c) It can detect leukaemic blast cells in peripheral blood in the acute phase of the disease. More importantly, it can detect residual leukaemic i.e. blast cells in peripheral blood even when the bone marrow picture is apparently normal (less than 5% blast cells still present, but not detectable by conventional methods), and hence can be used for detection of minimal residual disease (MRD);
  (d) The assay can assess response of ALL patients to chemotherapy and hence can also be used for determining drug sensitivity and the duration of treatment;
  (e) If performed with peripheral blood of follow-up patients, it can predict relapses;
  (f) It reflects the expression of a common maker, a 9-O AcSG, in ALL patients of different linkages, i.e. it can be used for different types of ALL (T cell ALL, B cell ALL and other types);
  (g) It can distinguish between different stages of acute lymphoblastic leukaemia which correlate well with the clinical status of the disease;
  (h) It detects the extent to which the patient has responded to chemotherapy;
  (i) Detects the percentage of recovery of individual ALL patients in response to chemotherapy
  (j) It shows no cross reactive response with other hematological disorder;
  (k) It requires no sophisticated instrument and minimum processing; and
  (i) Owing to low cost (~Rs 400) involved in this invention, it can be widely applied in any clinical laboratories of developing countries like India.

However, the lymphoproliferative assay by convention $^3$H-thymidine uptake has some disadvantages as it is a radiometric assay and it is necessary to harvest and wash the cells which increase the processing time.

In comparison, the colorimetric assay employing 3-(4,5-dimethylthiazole-2-yl)-2,5-diphenyltetrazolium bromide (MTT) is non radiometric and rapid since it is not necessary to harvest and wash the cells and the enzyme activity can be directly read on an automatic spectrophotometer or an ELISA plate reader (Mosman, 1983; Denizot, 1986; Tada, 1986; Kaspers 1995). However, owing to its dependence both on the number of cells and mitochondrial activity per cell type, each assay parameter was standardized to obtain optimal sensitivity and results compared with that of $^3$H-Thymidine uptake, the MTT assay can serve as an alternative readout for cellular growth and survival of lymphocytes in microcultures.

Other applications of the lectin

The lectin Achatinin-H, is a unique probe for identification of the cell surface marker "9-O-Acetylated sialoglycoconjugate". It has been utilised in two completely different systems, the common feature being the cell surface marker "9-O-Acetylated sialoglycoconjugate". The two diseases in question are (i) visceral leishmaniasis and (ii) acute lymphoblastic leukemia.

Clinically, the two disease processes are completely different from each other and are easily distinguishable as also the mode of treatment are totally different. With regard to the invention, the important differences are as follows:

1. In the proposed invention the diagnosis of visceral leishmaniasis is based on the presence of the biomarker "9-O-Acetylated sialoglycoconjugate" on erythrocytes whereas in acute lymphoblastic leukemia it is based on the presence of the biomarker "9-O-Acetylated sialoglycoconjugate" on peripheral blood mononuclear cells.
2. In the proposed invention the diagnosis of visceral leishmaniasis is based on the agglutination of erythrocytes using the lectin Achatinin-H whereas in acute lymphoblastic leukemia it is based on the lymphoproliferative assay using the lectin Achatinin-H.
3. The diagnosis of visceral leishmaniasis is based on the naked eye evaluation of agglutination of erythrocytes using the lectin Achatinin-H whereas in acute lymphoblastic leukemia it is based on the lymphoproliferative assay using the lectin Achatinin-H which is measured either by radiometric or colorimetric assay.
4. The haemagglutination assay is positive only during the acute phase of the disease in visceral leishmaniasis prior to treatment whereas in acute lymphoblastic leukemia the detection of minimal residual disease and prediction of relapse the proposed invention is of utmost importance after initial phase of chemotherapy.

We claim:

1. A method for diagnosing minimal residual disease and predicting its relapse in patients suffering from acute lymphoblastic leukaemia, comprising:
  a. collecting a blood sample from the patient suffering from acute lymphoblastic leukaemia;
  b. separating peripheral blood mononuclear cells from said blood sample;
  c. culturing the peripheral blood mononuclear cells in tissue culture medium with Achatinin-H;
  d. harvesting and counting the patient's mononuclear cells; and
  e. determining whether the patient's mononuclear cells have proliferated in response to culturing with Achatinin-H wherein the presence of minimal residual disease is associated with a level of proliferation greater than that exhibited by normal mononuclear cells cultured under the same conditions.

2. The method of claim 1, further comprising pulsing the cultures obtained in step (c) above with 1 $\mu$Ci of $^3$H-thymidine 18 hrs. before the termination of cultures.

3. The method of claim 2, further comprising:
  determining the optimal Achatinin-H concentration required for maximal proliferation of the patient's peripheral blood mononuclear cells, and comparing the concentration with that required for normal peripheral blood mononuclear cells, wherein mononuclear cells from a patient with minimal residual disease require a lower concentration of Achatinin-H for maximal proliferation than do normal mononuclear cells.

4. The method of claim 1, further comprising:
  pulsing the cultures obtained in step (c) with 3-(4,5-dimethylthiazole-2-yl)-2,5-diphenyltetrazolium bromide (MTT) for 4 hrs. at 37° C. before the termination of culturing;

adding a solvent to dissolve purple formazan crystals formed at the end of culturing;

measuring the amount of formazan colorimetrically; and using the colorimetric information to determine the optimal Achatinin-H concentration required for maximal proliferation of the patient's peripheral blood mononuclear cells and comparing the concentration with that required for normal peripheral blood mononuclear cells, wherein mononuclear cells from a patient with minimal residual disease require a lower concentration of Achatinin-H for maximal proliferation than do normal mononuclear cells.

5. The method of claim 4, wherein the optimal Achatinin-H concentration required for maximal proliferation of peripheral blood mononuclear cells increases with progress of chemotherapy.

6. The method of claim 4, where the measuring comprises determining the optimal density at 560 nm with a 690 nm reference in an ELISA reader.

7. The method of claim 4, wherein the solvent of is DMSO or SDS.

8. The method of claim 1, wherein blood sample of step a is whole blood.

9. The method of claim 1, wherein the concentration of Achatinin-H of step c ranges between 0.05–10 $\mu$g for stimulation of peripheral blood mononuclear cells.

10. The method of claim 1, wherein the culture medium of step c comprises RMPI 1640 supplemented with glutamine, antibiotics and 10% inactivated human antibody serum.

11. The method of claim 1, wherein the culture medium comprises DEM or fetal calf-serum.

12. The method of claim 1, wherein the culturing of step c is conducted in 96 well flat bottom microtitre plates selected from TARSON, NUNC, COSTER OR CORNING plates and sterile test tubes.

13. The method of claim 1, wherein the culturing of step c is done for 4 days.

14. The method of claim 1, wherein the culturing of step c is done in a carbon dioxide incubator for 4 days.

15. The method of claim 1, wherein reaction volume used to culture peripheral blood mononuclear cells ranges from 0.25 ml to 0.5 ml for the total reaction volume.

16. The method of claim 1, wherein the culturing of step c is at performed at 37° C. in the presence of Achatinin-H.

17. The method of claim 1, wherein the culturing of step c is performed in a humidified atmosphere of 5% $CO_2$ and 95% air.

18. The method of claim 1, wherein the culturing of step c comprises culturing the peripheral blood mononuclear cells as a concentration of $1 \times 10^5$ cells per well.

* * * * *